United States Patent [19]

Hartman

[11] 4,418,062

[45] Nov. 29, 1983

[54] AMINO DERIVATIVES OF CHLORO NITRO AMINO PYRAZINES USEFUL AS ADJUNCTS TO RADIATION THERAPY

[75] Inventor: George D. Hartman, Lansdale, Pa.

[73] Assignee: Merck & Co., Inc., Rahway, N.J.

[21] Appl. No.: 399,924

[22] Filed: Jul. 19, 1982

Related U.S. Application Data

[63] Continuation-in-part of Ser. No. 295,446, Aug. 24, 1981, abandoned, which is a continuation-in-part of Ser. No. 194,100, Oct. 6, 1980, abandoned.

[51] Int. Cl.³ .................. A61K 31/495; C07D 241/16; C07D 241/20
[52] U.S. Cl. .................................. 424/248.4; 424/250; 544/405; 544/120; 544/359
[58] Field of Search ....................... 544/409, 120, 359; 424/250, 248.4

[56] References Cited

U.S. PATENT DOCUMENTS 3,541,093 11/1970 Tull et al. .............................. 544/405
3,660,397 2/1972 Jones et al. ........................ 137/246.12

FOREIGN PATENT DOCUMENTS 1232758 5/1971 United Kingdom ................ 544/405

OTHER PUBLICATIONS

Ainsworth, et al., *Canadian J. Biochemistry* 56: (1978) pp. 457–461.
Adams, et al., *The Lancet*, (Jan., 1976) pp. 186–188.
Olive, Peggy; *Cancer Research* vol. 39 (Nov. 1979) pp. 4512–4515.
Anderson, et al., *British J. of Cancer*, vol. 37, (1978) pp. 103–106.

*Primary Examiner*—Mark L. Berch
*Assistant Examiner*—G. Hendricks
*Attorney, Agent, or Firm*—Thomas E. Arther; Mario A. Monaco

[57] ABSTRACT

2-Substituted amino derivatives of 6-amino-3-chloro-5-nitropyrazin-2-yl are prepared by converting 3-amino-5,6-dichloropyrazinecarboxylic acid to 5,6-dichloro-3-nitropyrazinamine and treating said compound with an amine to produce the corresponding 2-substituted amino compound.

10 Claims, No Drawings

AMINO DERIVATIVES OF CHLORO NITRO AMINO PYRAZINES USEFUL AS ADJUNCTS TO RADIATION THERAPY

BACKGROUND OF THE INVENTION

This application is a continuation-in-part of copending application Ser. No. 295,446, filed Aug. 24, 1981, now abandoned, which in turn is a continuation-in-part of copending U.S. application Ser. No. 194,100 filed Oct. 6, 1980 and now abandoned.

This invention relates to substituted derivatives of 6-amino-3-chloro-5-nitropyrazinamino compounds and the acid addition salts thereof, used to selectively sensitize tumor cells to therapeutic radiation and thus increase the effective therapeutic ratio of radiologic treatment. This invention also relates to the process of preparing such compounds by first converting 3-amino-5,6-dichloropyrazine carboxylic acid by nitration in sulfuric/nitric acid to 5,6-dichloro-3-nitropyrazinamine and subsequently treating said 5,6-dichloro-compound in the presence of a base such as a tertiary amine to produce the desired 2-substituted compounds and if desired, converting said 2-substituted pyrazines to the acid addition salts thereof. In addition, the present invention relates to pharmaceutical compositions comprising such pyrazine compounds and to methods of treatment comprising administering such compounds to patients undergoing radiation therapy to enhance the effectiveness of such treatment.

At the present time, certain other unrelated compounds are in experimental clinical use as radiation sensitizers. However, these compounds—for example, metronidazole and misonidazole—suffer from the drawback that they also cause symptoms of neurotoxicity which limits their usefulness. The compounds of the present invention are effective radiation sensitizers, but are believed to have a more favorable therapeutic ratio.

DETAILED DESCRIPTION OF THE INVENTION

The compositions of the present invention which are useful as radiation sensitizers are 2 substituted derivatives of 6-amino-3-chloro-5-nitropyrazine and the acid addition salts thereof of the formula:

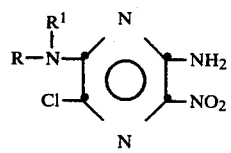

wherein R and R$^1$ are each hydrogen, a saturated or unsaturated alkyl substituent of from 1–6 carbon atoms, substituted alkyl substituents in which one or more of the alkyl hydrogens is replaced by hydroxy, alkoxy, carboalkoxy, phenyl, pyrimidinyl, pyridyl or imidazolyl or when taken together along with the nitrogen atom to which they are attached represent a 6-membered heterocyclic ring including morpholine, piperazine and N-lower alkyl piperazine in combination with a pharmaceutical carrier.

A preferred subgroup of novel compounds of the present invention are represented by the following structural formula:

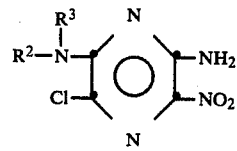

wherein R$^2$ and R$^3$ are each individually hydrogen, lower alkyl groups substituted by hydroxy, halo including fluoro, chloro or bromo, or lower alkanoyl substituted by one or more hydroxy groups, provided that at least one of R$^2$ and R$^3$ is a substituent other than hydrogen and the corresponding acid addition salts formed by reaction of the above amino compound with an equimolar amount of a strong mineral acid such as hydrochloric acid, hydrobromic acid, sulfuric and phosphoric acids.

The amines described above are prepared from the known 3-amino-5,6-dichloropyrazine carboxylic acid E. J. Cragoe, Jr., O. W. Woltersdorf, Jr., J. B. Bicking, S. F. Kwong, J. H. Jones, *J. Med. Chem.*, 10, 66 (1967). The carboxylic acid is dissolved in sulfuric acid or fuming sulfuric acid. To the solution formed in this manner, a mixture of equal volumes of sulfuric and nitric acid or the corresponding fuming sulfuric and fuming nitric acids are added to the solution to effect replacement of the carboxylic acid substituent by a nitro-substituent. The nitric and sulfuric acids are used in approximately equimolar amounts to the carboxylic acid reagent. Preferably, however, these acids are used in from 10–100% molar excess. The reaction temperature is maintained between 0° and 50° C. for a period of 0.5 to 5.0 hours. The progress of the reaction is followed by observation of the evolution of carbon dioxide from the reaction mixture. This reaction is illustrated in the following reaction scheme:

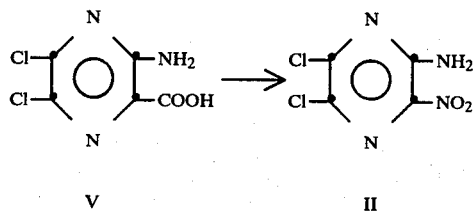

The product is conveniently recovered from the reaction mixture by pouring the entire mixture onto ice whereupon the product is precipitated as a crude yellow solid. Further purification is effected by dissolving the crude product in a solvent such as ethyl acetate and washing with an alkaline solution such as aqueous sodium carbonate to remove traces of acid. The solution of product is then filtered to remove insoluble impurities and the product recovered from the filtrate by evaporation of solvent leaving substantially pure product as a solid residue.

Compound II hereinabove is then treated with an amine compound to replace the chloro-substituent as illustrated hereinbelow:

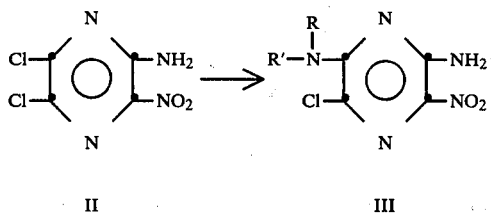

The reaction of the dichloro-nitropyrazine II with the amine reagent is preferably carried out in a solvent for the reactant. The solvent employed is a lower alkanol such as methanol, ethanol, isopropanol; esters such as tetrahydrofuran; dimethyl formamide; and acetonitrile. The amine reactant is preferably present in approximately a 5–10% molar excess over the nitropyrazine. The reagents are first mixed and then preferably heated to a temperature of 20°–80° C. for a period of from 0.5 to 24 hours. In addition to the reagents and the solvent it is generally preferred to carry out the reaction in the presence of at least an equimolar amount of an organic base. Tertiary amines such as triethylamine and pyridine are preferred. The progress of the reaction is followed by the use of thin layer chromatography.

As indicated hereinabove acid addition salts of compounds of Formula I may be prepared by mixing a selected compound of Formula I with an equimolar amount of a strong mineral acid in a solvent for the reactants at a temperature of 0° to 50° C. Solvents preferred are lower alkanols such as methanol, ethanol, isopropanol. The salt is precipitated from the alcoholic solution, filtered, washed with a minimal amount of cold alcohol and air dried.

The method of treatment of human patients or domestic animals undergoing radiation treatment of malignant disease processes employs the compounds of the present invention in pharmaceutical compositions that are administered orally or parenterally, preferably intravenously. The dose employed depends on the radiation protocol for each individual patient. In protocols where the radiation dose is divided into a large number of fractions, the drug can be administered at intervals in the schedule and not necessarily with each radiation treatment. It should be noted that the compounds of the present invention are not intended for chronic administration. In general, the drug is administered from 10 minutes to 5 hours prior to the radiation treatment in a dosage amount of between 0.25 to about 4.0 grams per square meter of body surface, approximately equivalent to a dosage of 6 to 100 mg/kg of patient body weight as set forth in the "Nelson Textbook of Pediatrics" Eleventh Edition (1979) p. 31, edited by Vaughan, McKay, Behrman, and Nelson.

The dosage range given is the effective dosage range and the decision as to the exact dosage used must be made by the administering physician based on his judgement of the patient's general physical condition. In determining the dose for the individual patient, the physician may begin with an initial dose of 0.25 g/square meter of body surface to determine how well the drug is tolerated and increase the dosage with each succeeding radiation treatment, observing the patient carefully for any drug side effect. The composition to be administered is an effective amount of the active compound and a pharmaceutical carrier for said active compound.

The dosage form for intravenous administration is a sterile isotonic solution of the drug. Oral dosage forms such as tablets, capsules, or elixirs are preferred.

Capsules or tablets containing from 25, 50, 100 or 500 mg of drug/capsule or tablets are satisfactory for use in the method of treatment of our invention.

For tablets or capsules the substantially pure compound may be combined with a pharmaceutically acceptable solid diluent or in the case of capsules filled directly into an appropriately sized capsules.

The following examples are intended to illustrate but do not limit the process of preparation, product, compositions, or method of treatment aspects of the invention.

EXAMPLE 1

2[(6-Amino-3-chloro-5-nitropyrazin-2-yl)amino]ethanol

STEP A: Preparation of 5,6-dichloro-3-nitropyrazinamine (II)

To 450 ml concentrated sulfuric acid cooled to 10° is added 50.0 g (0.2 m) 3-amino-5,6-dichloropyrazine carboxylic acid. To this solution cooled to 0°–520, is added a cold solution of 15 ml fuming sulfuric acid in 15 ml fuming nitric acid dropwise over 15 minutes. The reaction mixture is stirred at 0°–5° for 2 hours and then at ambient temperature for 2 hours. The reaction mixture is then poured onto ice and the yellow solid is collected. This solid is taken up in ethyl acetate, washed twice with saturated sodium carbonate solution and then the solution is filtered through a pad of silica gel. The resulting solution is evaporated in vacuo to afford 35 g of 5,6-dichloro-3nitropyrazinamine, m.p. 169°–170° C.

STEP B: Preparation of 2[(6-Amino-3-chloro-5-nitropyrazin-2yl)amino]ethanol

To 1.0 g of 5,6-dichloro-3-nitropyrazinamine in 20 ml isopropanol is added 0.5 ml triethylamine and then 0.3 ml 2-aminoethanol. The reaction mixture is stirred for 3 hours and then concentrated in vacuo to solids. The solids are triturated with hot chloroform and recrystallized from acetonitrile to afford 0.6 g of 2[(6-Amino-3-chloro-5-nitropyrazin-2-yl)amino]ethanol, m.p. 196°–197° C.

Employing the procedure substantially as described in Example 1, but employing in Step B the appropriate amine, there are produced:

| Example | Reagent | Product | m.p. |
| --- | --- | --- | --- |
| 2 | diethanolamine | 2-[(6-amino-3-chloro-5-nitro-pyrazin-2-yl)amino]-di-ethanol | 194–196° C. |
| 3 | 2-amino-2-methyl-1,3-crotonate | 2-[(6-amino-3-chloro-5-nitro-pyrazin-2-yl)amino]-2-methyl-1,3-propanediol | 214–215° C. |
| 4 | 3-amino-1,2-propanediol | 3-[(6-amino-3-chloro-5-nitro-pyrazin-2-yl)amino]-1,2-propanediol | 202–204° C. |
| 5 | morpholine | N—(6-amino-3-chloro-5-nitro-pyrazin-2-yl)-morpholine | 211–212° C. |
| 6 | aniline | N—(6-amino-3-chloro-5-nitro-pyrazin-2-yl)-aniline | 236–237° C. |
| 7 | N—methyl-ethanolamine | 2-[(6-amino-3-chloro-5-nitro- | 166–167° C. |

-continued

| Example | Reagent | Product | m.p. |
|---|---|---|---|
| 8 | Ethyl 3-amino-crotonate | pyrazin-2-yl)amino]-N—methyl ethanol Ethyl 3-[(6-amino-3-chloro-5-nitro-pyrazin-2-yl)amino]-crotoante | 162–163° C. |
| 9 | 4-Methyl piperazine | 5-Chloro-6-(4-methyl-1-piperazinyl)-3-nitropyrazine amine | 186–188° C. |
| 10 | 2-(dimethylamino) ethyl amine | 5-Chloro-6[2-(dimethylamino)-ethyl amino]3-nitropyrazine amine | |

EXAMPLE 11

Sterile Isotonic Solutions for Injection

Suitable formulations for injection are prepared by dissolving each of the compounds of Examples 1–10 inclusive in isotonic solution in a concentration of about 1 mg/ml and sterilizing the resulting solution. It is suitable for intravenous injection.

EXAMPLE 12

Capsules

Suitable formulations for oral administration are prepared by filling appropriately sized capsules individually with 25 and 50 mg portions of each of the compounds produced in accordance with Examples 1–10 inclusive.

EXAMPLE 13

| Tablet Formulation | |
|---|---|
| Ingredients | Amount |
| Product of any of Examples 1–10 | 25 mg |
| Calcium phosphate | 120 mg |
| Lactose | 50 mg |
| Starch | 23 mg |
| Magnesium Stearate | 1 mg |

What is claimed is:

1. A pharmaceutical composition useful in enhancing the therapeutic effect of radiation treatment comprising an effective amount of a radiation enhancing compound of the formula

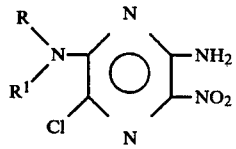

wherein R and $R^1$ are each $C_1$–$C_6$ loweralkyl and substituted lower alkyl having one or two amino $C_1$ lower alkylamino or dialkylamino, lower alkoxy, hydroxy or halo $C_1$–$C_6$ loweralkenyl, and substituted lower alkenyl having one or two amino, $C_1$–$C_6$ alkylamino or dialkylamino, loweralkoxy, or hydroxy groups or when taken together and linked through an additional nitrogen or oxygen constitutes a 5–7 member saturated heterocyclic ring comprising a morpholine, a piperazine or an N-substituted piperazine wherein the N-substituent is either hydrogen, $C_1$–$C_6$ alkyl, $C_1$–$C_6$ hydroxyalkyl, $C_1$–$C_6$ alkoxyalkyl and a pharmaceutical carrier.

2. A composition according to claim 1 wherein the radiation enhancing compound is 2-[(6-amino-3-chloro-5-nitropyrazin-2-yl)amino]ethanol.

3. A composition according to claim 1 wherein the radiation enhancing compound is 2-[(6-amino-3-chloro-5-nitropyrazin-2-yl)amino] di-ethanol.

4. A composition according to claim 1 wherein the radiation enhancing compound is 2-[(6-amino-3-chloro-5-nitropyrazin-2-yl)amino]-2-methyl-1,3-propanediol.

5. A composition according to claim 1 wherein the radiation enhancing compound is 3-[(6-amino-3-chloro-5-nitropyrazin-2-yl)amino]-1,2-propanediol.

6. A composition according to claim 1 wherein the radiation enhancing compound is N-(6-amino-3-chloro-5-nitropyrazin-2-yl)morpholine.

7. A composition according to claim 1 wherein the radiation enhancing compound is N-(6-amino-3-chloro-5-nitropyrazin-2-yl)aniline.

8. A composition according to claim 1 wherein the radiation enhancing compound is 2-[(6-amino-3-chloro-5-nitropyrazin-2-yl)amino]-N-methyl ethanol.

9. A method of enhancing the therapeutic effect of radiation treatment which comprises administering to a patient in need of such radiation treatment an effective sensitizing amount of a compound having the formula:

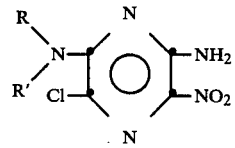

wherein R and R' are as defined in claim 1.

10. A pyrazine compound of the formula

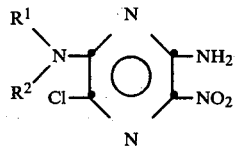

wherein $R^1$ and $R^2$ are each lower alkyl substituted with one or two hydroxy or halogen groups including fluoro, chloro, bromo or lower alkenyl substituted with one or two hydroxy groups.

* * * * *